(12) United States Patent
Venkitachalam et al.

(10) Patent No.: US 12,409,153 B2
(45) Date of Patent: Sep. 9, 2025

(54) LIQUID INJECTABLE COMPOSITION

(71) Applicant: AMATERASU LIFESCIENCES LLP, Mumbai (IN)

(72) Inventors: Padma Venkitachalam, Mumbai (IN); Shilpa Mahesh Dawre, Mumbai (IN)

( * ) Notice: Subject to any disclaimer, the term of this patent is extended or adjusted under 35 U.S.C. 154(b) by 940 days.

(21) Appl. No.: 17/289,008

(22) PCT Filed: Nov. 1, 2019

(86) PCT No.: PCT/IN2019/050808
§ 371 (c)(1),
(2) Date: Apr. 27, 2021

(87) PCT Pub. No.: WO2020/089942
PCT Pub. Date: May 7, 2020

(65) Prior Publication Data
US 2021/0401775 A1 Dec. 30, 2021

(30) Foreign Application Priority Data
Nov. 2, 2018 (IN) .............................. 201821041493

(51) Int. Cl.
| | | |
|---|---|---|
| *A61K 31/137* | (2006.01) | |
| *A61K 9/00* | (2006.01) | |
| *A61K 31/357* | (2006.01) | |
| *A61K 47/12* | (2006.01) | |
| *A61K 47/14* | (2017.01) | |
| *A61K 47/26* | (2006.01) | |
| *A61K 47/32* | (2006.01) | |

(52) U.S. Cl.
CPC .......... *A61K 31/137* (2013.01); *A61K 9/0019* (2013.01); *A61K 31/357* (2013.01); *A61K 47/12* (2013.01); *A61K 47/14* (2013.01); *A61K 47/26* (2013.01); *A61K 47/32* (2013.01)

(58) Field of Classification Search
CPC .. A61K 31/137; A61K 9/0019; A61K 31/357; A61K 47/12; A61K 47/14; A61K 47/26; A61K 47/32; A61K 9/0024; A61K 9/06; A61K 9/1075; A61K 31/366; A61K 47/22; A61K 47/34; A61K 47/44; Y02A 50/30
See application file for complete search history.

(56) References Cited

U.S. PATENT DOCUMENTS

| | | | | |
|---|---|---|---|---|
| 4,784,845 A | * | 11/1988 | Desai ..................... | A61K 47/44 514/939 |
| 6,245,349 B1 | * | 6/2001 | Yiv ..................... | A61K 9/1075 514/393 |
| 2010/0137844 A1 | * | 6/2010 | Hyde .................. | A61K 31/4725 604/891.1 |
| 2016/0022583 A1 | | 1/2016 | Lee et al. | |
| 2018/0055941 A1 | | 3/2018 | Kaneko et al. | |

FOREIGN PATENT DOCUMENTS

| | | | | |
|---|---|---|---|---|
| WO | WO-9801117 A1 | * | 1/1998 | ........... A61K 31/192 |
| WO | 2000024374 A1 | | 5/2000 | |
| WO | 2005002625 A3 | | 4/2005 | |
| WO | 2010082219 A3 | | 11/2010 | |

OTHER PUBLICATIONS

Dawre et al. Enhanced antimalalarial activity of a prolonged release in situ gel of arteether-lumefantrine in a murine model, (European Journal of Pharmaceutics and Biopharmaceutics, 123, 95-107). (Year: 2018).*
Dawre et al. Enhanced antimalalarial activity of a prolonged release in situ gel of arteether-lumefantrine in a murine model (European Journal of Pharmaceutics and Biopharmaceutics, 123, 95-107) pub: Nov. 6, 2017 (Year: 2018).*
Malik et al. Atrigel: A potential parenteral controlled drug delivery system, (Der Pharmacia Sinica, 1(1): 74-81) (Year: 2010).*
PubChem (Methylpyrrolidone) (Year: 2004).*
Kokwaro et al. Artemether/lumefantrine in the treatment of uncomplicated falciparum malaria (Expert Opin. Pharmacother. (1) (Year: 2007).*
Variations (The Royal Statistical Society, p. 47-48) (Year: 2014).*
Handbook of Pharmaceutical Excipients, 8th Rev. Edition, American Pharmacists Association (APhA), Raymond C. Rowe (Editor) (2005).
Dawre, S, et al. "Enhanced Antimalalarial Activity of a Prolonged Release in Situ Gel of Arteether-Lumefantrine in a Murine Model" Eur. J. Pharm. Biopharm Feb. 2018., vol. 123, pp. 95-107.
International Search Report and Written Opinion of the International Searching Authority, PCT/IN2019/50808, mailed Jun. 16, 2020, 12 pages.
Malik K, et al. "Atrigel: A potential parenteral controlled drug delivery system" Der Pharmacia Sinica 2010, vol. 1, No. 1. pp. 74-81.

* cited by examiner

*Primary Examiner* — Joseph K McKane
*Assistant Examiner* — Meghan C Heasley
(74) *Attorney, Agent, or Firm* — Carlson, Caspers, Vandenburgh & Lindquist, P.A.

(57) ABSTRACT

A liquid injectable composition comprising (a) at least one surfactant; (b) at least one gel strength enhancer; (c) at least one solvent; (d) optionally release retarding agent(s); (e) optionally stabilizing agent(s); (f) optionally pharmaceutical excipient(s); and (g) active pharmaceutical ingredient(s) (API) and its use in treating a subject suffering from a disease or disorder.

9 Claims, 6 Drawing Sheets
(2 of 6 Drawing Sheet(s) Filed in Color)

Figure 1: Polarization optical microscopy photographs A. example -3.1; B. example -3.1 gel; C. example -3.2; D. example-3.2 gel; E. example-3.3; F. example-3.3 gel; G. example-3.4; H. example-3.4 gel.

Figure 2: In situ gelling in EDL muscle of Gallus gallusdomesticus A. example 3.1; B. example 3.2; C. example 3.3; D. example 3.4

Figure 3: A. Arteether release from arteether-lumefantrinesolution, example 3.1 and example 3.2; B. Lumefantrine release from arteether-lumefantrinesolution, example 3.1 and example 3.2

Figure 4: A. Arteether release from arteether-lumefantrine solution, example 3.3 and example 3.4; B. Lumefantrine release from arteether-lumefantrinesolution, example 3.3 and example 3.4

Figure 5: Parasitemia count for control, marketed product at 100% therapeutic dose at multiple doses, Example 3.2 at 1/20th, 1/40th, 1/80th of therapeutic dose administered as single dose therapy in clinical simulation study Figure 6: Survival plot for control, marketed product at 100% therapeutic dose at multiple doses, Example 3.2 at 1/20th, 1/40th, 1/80th of therapeutic dose administered as single dose therapy in clinical simulation study Figure 7: Antimalarial activity of drug solution, examples 3.11 and 3.12 at 1/10th of therapeutic dose administered as single dose therapy, marketed product at 100% therapeutic dose at multiple doses in clinical simulation study Figure 8: Survival of placebo of example 3.11, drug solution, examples 3.11 and 3.12 at 1/10th of therapeutic dose administered as single dose therapy, marketed product at 100% therapeutic dose at multiple doses, in clinical simulation study Figure 9: Gel formation for example 4.1, 4.2, 4.3, 4.4 and 4.5 at T=0 (A), T=5h (B) T=46h(C) and T=70h (D)

Figure 10: In vitro release profile of donepezil base from example 4.1, 4.2, 4.3, and 4.5

LIQUID INJECTABLE COMPOSITION

CROSS-REFERENCE TO RELATED APPLICATIONS

This application is a 35 U.S.C. § 371 National Stage Application of PCT/IN2019/050808, filed Nov. 1, 2019, which claims the benefit of priority to Serial No. IN201821041493, filed on Nov. 2, 2018 in India, the disclosures of which are incorporated herein by reference in their entirety.

BACKGROUND OF THE INVENTION

Biologically active agents may be incorporated in a number of different dosage forms for administration by a number of different routes. These dosage forms may be for example tablets, capsules, sprays, ointments or patches for delivery of the active agent by routes such as oral, transmucosal or transdermal routes. However, for a variety of reasons many biologically active agents may not be effectively delivered using routes such as oral, transmucosal or transdermal routes. This may be because the biologically active agent is susceptible to degradation by enzymes or stomach acid, or is insufficiently absorbed into the systemic circulation due to hydrophobic nature, molecular size and/or charge.

Hence, a number of biologically active agents are most suitably administrated by injection. Administration by injection allows an active agent to rapidly enter the systemic circulation and to by-pass the digestive system and first-pass metabolism by the liver. However, repeated injections of an active agent over a period of time may be necessary in order to achieve or maintain a desired effect in vivo.

Controlled release compositions are of interest in biomedical applications wherein maintenance of a systemic level of an active agent over a period of time is desired. For injected biologically active agents, controlled release compositions can help to reduce the frequency of injection and increase the duration of action of the active agent or reduce adverse side effects. A number of injectable controlled release compositions have been described. For example, one form of injectable sustained release composition utilises small diameter polymer particles for the delivery of an encapsulated drug. Such polymer particles are often formed from synthetic degradable polymers such as poly(lactic acid), poly(glycolic acid) or poly(lactic-co-glycolic acid), which breakdown in a biological environment, leading to release of the encapsulated drug over an extended period of time. Drug release may therefore be reliant on the rate of breakdown of the polymer, which may not always give a desired kinetic profile.

Patient compliance with a dosing regimen is difficult to ensure, especially where the course of therapy is long or of indeterminate or lifetime duration. There is a need for methods to deliver these drugs more effectively, so that therapeutic concentrations are maintained constantly in the tissues intended to be treated over an extended period of time, with minimal vulnerability to the vagaries of patient compliance, and ideally with minimal systemic exposure or exposure of uninvolved tissues and organs. Modern drug discovery methods have led to the development of many drugs which are far more potent, yet have poorer solubility, than drugs developed through traditional medicinal chemistry methods. The development of these often-complex drugs has resulted in a need for methods to deliver such drugs more effectively and efficiently as well.

There remains a need to develop an injectable composition that can provide a desired release profile for a biologically active agent and through a single dose therapy.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed before the priority date of each claim of this application.

RELATED ART

PCT publication WO 2010/82219 (applicant Lincoln Pharmaceuticals Limited) discloses an injectable formulation for the treatment of malaria comprising Arteether, ethyl alcohol, benzyl alcohol, butylated hydroxyl toluene, butylated hydroxyl toluene, butylated hydroxyl anisole, propyl gallate and ethyl oleate. The invention discloses non gel forming, non controlled release, low viscous injectable of Arteether. However, one of the embodiment the present invention is an intramuscular combination of arteether and lumefantrine, artemether and lumefantrine in situ gel forming solution to enable controlled release of drugs for single dose therapy.

US publication 2016/0022583 (applicant Dongkook Pharmaceutical Co. Ltd.) discloses a parenteral donepezil microsphere composition comprising a biodegradable, biocompatible polymer. However, one of the embodiments of the present invention is a solution.

PCT publication WO 2000/024374 (applicant Atrix Laboratories, Inc.) is related to controlled release liquid delivery compositions with low initial drug burst which discloses use of polymeric controlled release additive (PLGA/PEG-5000, PEG 400 monostearate, Pluronics F127) for burst release control. However, one of the embodiments of the present invention uses lipophilic agent to reduce burst release.

PCT publication WO 2005/002625 (applicant Control Delivery Systems, Inc.) discloses an injectable pharmaceutical composition comprising: (a) a drug substance; (b) a polyethylene glycol; and (c) a biocompatible and bioerodible poly(DL-lactide-glycolide) (PLGA) polymer; wherein the bioerodable PLGA polymer is dissolved, dispersed or suspended in the polyethylene glycol. However, the composition of the present invention does not comprise polyethylene glycol.

SUMMARY

The present invention provides for a liquid injectable composition that includes: (a) at least one surfactant; (b) at least one gel strength enhancer; (c) at least one solvent; (d) optionally, release retarding agent(s); (e) optionally stabilizing agent(s); (f) optionally pharmaceutical excipient(s); and (g) active pharmaceutical ingredient(s) (API).

The present invention also provides for a composition which is a unit dosage form of about 400-4,000 mcL, the composition includes arteether and lumefantrine.

The present invention also provides for a composition which is a unit dosage form of about 400-4,000 mcL, the composition includes artemether and lumefantrine.

The present invention also provides for a method of treating a subject suffering from a disease or disorder ameliorated by one or more active pharmaceutical ingredients, the method including administering a liquid injectable composition that includes: (a) at least one surfactant; (b) at least one gel strength enhancer; (c) at least one solvent; (d) optionally release retarding agent(s); (e) optionally stabilizing agent(s); (f) optionally pharmaceutical excipient(s); and (g) active pharmaceutical ingredient(s) (API), in an amount and for a period of time sufficient to treat the subject.

The present invention provides an injectable composition comprising a biologically active agent that is formulated to provide for initial rapid release of the biologically active agent, followed by sustained delivery of the biological active agent, to a subject in vivo.

The present invention provides a controlled release liquid injectable composition which can be administered as a single or multiple dose therapy. The single dose therapy can reduce or obviate the need for repeated dosing.

The injectable composition of the present invention is useful for the delivery of a wide range of biologically active agents.

The present invention further provides a method of treating or preventing a disease or disorder in a subject comprising the step of administering an injectable composition of any one of the embodiments described herein to the subject by injection.

In one embodiment, the injectable composition may be suitably used for the treatment or prevention of malaria.

In another embodiment, the injectable composition may be suitably used for the treatment or prevention of a viral infection, bacterial infection, fungal infection, parasitic infection or any form of infection.

In another embodiment, the injectable composition may be suitably used for the treatment or prevention of disease of nervous system.

In another embodiment, the injectable composition may be suitably used for the treatment or prevention of Alzheimers or dementia.

In another embodiment, the injectable composition may be suitably used for the treatment or prevention of Parkinson's disease.

In another embodiment, the injectable composition may be suitably used as a contraceptive.

In another embodiment, the injectable composition may be suitably used for the treatment or prevention of ophthalmic ailments.

In another embodiment, the injectable composition may be suitably used for the treatment or prevention of cardiovascular diseases.

In another embodiment, the injectable composition may be suitably used for the treatment or prevention of endocrine disorders.

In another embodiment, the injectable composition may be suitably used for pain management.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION

I. Introduction

The present invention is based, in part, upon the discovery of novel liquid injectable compositions (and unit dosage forms containing the same), that provide advantages when used for the in vivo delivery of an active or therapeutic agent, resulting in a significant increase in the therapeutic index as compared to other compositions (and unit dosage forms) containing the same active or therapeutic agent. In specific embodiments, the liquid injectable composition (as a unit dosage form containing the same) can be administered in a single dose or multiple doses, which effectively treats the disease or disorder.

II. Definitions

As used herein, the following terms have the meanings ascribed to them unless specified otherwise.

The term "surfactant" refers to a substance that lowers the surface tension (or interfacial tension) between two liquids, between a gas and a liquid, or between a liquid and a solid. Surfactants may act as detergents, wetting agents, emulsifiers, foaming agents, and/or dispersants.

The term "non-ionic surfactant" refers to surfactants that have covalently bonded oxygen-containing hydrophilic groups, which are bonded to hydrophobic parent structures. The water-solubility of the oxygen groups is the result of hydrogen bonding. Hydrogen bonding decreases with increasing temperature, and the water solubility of nonionic surfactants therefore decreases with increasing temperature.

Non-ionic surfactants are less sensitive to water hardness than anionic surfactants, and they foam less strongly.

A "lyotropic liquid crystalline phase" is formed by dissolving an amphiphilic mesogen in a suitable solvent, under appropriate conditions of concentration, temperature and pressure.

The term "gel" refers to a solid jelly-like material that can have properties ranging from soft and weak to hard and tough. Gels are defined as cross-linked system, which exhibits no flow when in the steady-state. By composition gels are mostly liquid, yet they behave like solids due to a three-dimensional network within the liquid. In this way gels are a dispersion of molecules of a liquid within a solid in which liquid particles are dispersed in the solid medium.

The term "gel strength enhancer" refers to a substance that increases the strength of a gel or aids in the formation of a gel.

The term "solvent" refers to a substance that dissolves a solute (a chemically distinct liquid, solid or gas), resulting in a solution. The solvents are grouped into nonpolar, polar aprotic, and polar protic solvents, with each group ordered by increasing polarity.

The term "release retarding agent" refers to a substance that inhibits the release of active pharmaceutical ingredient from the composition, e.g., after it is administered to the subject and the composition forms a depot in situ. Use of the release retarding agent can decrease a burst effect of the active pharmaceutical ingredient from the composition. Additionally, use of the release retarding agent can increase the time in which the active pharmaceutical ingredient is released from the composition.

The term "stabilizing agent" refers to a substance that increases the stability of a composition, including the specific compounds present therein.

The term "pharmaceutical excipient" refers to substance formulated alongside the active ingredient of a medication, included for the purpose of long-term stabilization, or to confer a therapeutic enhancement on the active ingredient in the final dosage form, such as facilitating drug absorption, reducing or increasing viscosity, or enhancing solubility. Excipients can also be useful in the manufacturing process, to aid in vitro stability such as prevention of decomposition or oxidation over the expected shelf life.

The term "active pharmaceutical ingredient" refers to the ingredient in a pharmaceutical drug or dosage form that is biologically active. Some medication products may contain more than one active ingredient. In contrast with the active ingredients, the inactive ingredients are usually called excipients in pharmaceutical contexts. The main excipient that serves as a medium for conveying the active ingredient is usually called the vehicle.

The term "unit dosage form" refers to the medication described herein (e.g., injectable composition), containing the active pharmaceutical ingredient (API) and excipients, formulated and configured for administration to the subject.

The term "ready to inject dosage form" refers to an injectable dosage form that does not require additional steps otherwise required to administer the medication. For example, a prefilled syringe is considered to be a ready to inject dosage form as it does not require introducing the medication in the syringe, as it is already contained therein.

The term "single dose therapy" refers to a unit dosage form (e.g., injectable composition), formulated and configured for administration, such that the single dose effectively treats the subject. The term "multiple dose" refers to administering the unit dosage form more than once.

The term "self microemulsifying drug delivery system (SMEDDS)" refers to a drug delivery system wherein a microemulsion is achieved by simple dilution of the drug formulation with an aqueous medium. That is, by an intrinsic property of the drug formulation, rather than by special mixing and handling.

The term "microemulsion" refers to clear, thermodynamically stable, isotropic liquid mixtures of oil, water and surfactant, frequently in combination with a cosurfactant. The aqueous phase may-contain salt(s) and/or other ingredients, and the "oil" may actually be a complex mixture of different oils from among triglycerides, diglycerides and monoglycerides of fatty acids or other liquid lipophilic agents. In contrast to ordinary emulsions, microemulsions form upon simple mixing of the components and do not require the high shear conditions generally used in the formation of ordinary emulsions. The three basic types of microemulsions are direct (oil dispersed in water, o/w), reversed (water dispersed in oil, w/o) and bicontinuous.

The term "depot" or "drug depot" refers to a mass of drug that is injected or implanted in the body, winch releases the API slowly, after which it erodes by bodily fluids and is slowly-absorbed into the circulation.

The term "in situ" refers to the formation of a product (e.g., depot) in the area of the body in which the composition is introduced.

The term "modified release" refers to a mechanism that (in contrast to immediate-release dosage) delivers an active ingredient with a delay after its administration (delayed-release dosage) or for a prolonged period of time (extended-release [ER, XR, XL] dosage) or to a specific target in the body (targeted-release dosage).

The term "sustained release" refers to dosage forms designed to release (liberate) an active ingredient at a predetermined rate in order to maintain a constant active ingredient concentration for a specific period of time with minimum side effects.

"Extended release" consists of sustained-release (SR) and controlled-release (CR) dosage. SR maintains drug release over a sustained period but not at a constant rate. CR maintains drug release over a sustained period at a nearly constant rate.

The term "vial" refers to a small glass or plastic vessel or bottle, often used to store medication as liquids, powders, tablets or capsules.

The term "syringe" refers to a simple reciprocating pump consisting of a plunger (though in modern syringes it's actually a piston) that fits tightly within a cylindrical tube called a barrel. The plunger can be linearly pulled and pushed along the inside of the tube, allowing the syringe to take in and expel liquid or gas through a discharge orifice at the front (open) end of the tube. The open end of the syringe may be fitted with a hypodermic needle, a nozzle or a tubing to help direct the flow into and out of the barrel. Syringes are frequently used in clinical medicine to administer injections, infuse intravenous therapy into the bloodstream, apply compounds such as glue or lubricant, and draw/measure liquids.

The term "prefilled syringe" refers to a syringe containing the medication (e.g., injectable composition). Such a syringe (containing the medication) can be commercially available and as such can be packaged accordingly.

The term "intramuscular" or "IM" refers to the injection of a substance directly into muscle. In medicine, it is one of several alternative methods for the administration of medications. Muscles have larger and more blood vessels than subcutaneous tissue and injections here usually have faster rates of absorption than subcutaneous injections or intradermal injections.

The term "subcutaneous" or "SC" refers to the administration as a bolus into the subcutis, the layer of skin directly below the dermis and epidermis, collectively referred to as the cutis. Subcutaneous injections are highly effective in administering medications.

The term "treating" (and equivalent terms such as "treat," "treated," and "treatment") of a subject includes the administration of a composition or unit dosage form described herein, to a subject with the purpose of preventing, curing, healing, alleviating, relieving, altering, remedying, ameliorating, improving, stabilizing or affecting a disease or disorder, or a symptom of a disease or disorder (e.g., to treat malaria).

The term "subject" refers to living organisms such as humans. Administration of the composition or unit dosage form described herein can be carried out at dosages effective for the treatment of the subject.

III. Liquid Injectable Compositions

The present invention provides, inter alia, novel liquid injectable compositions and unit dosage forms containing the same. The liquid injectable composition (or unit dosage form containing the same) can be formulated as a single dose therapy unit dosage form. In specific embodiments, the liquid injectable composition (as a unit dosage form containing the same) can be administered in a single dose or multiple doses, which effectively treats the disease or disorder.

As described in detail herein, the liquid injectable composition includes: (a) at least one surfactant; (b) at least one gel strength enhancer; (c) at least one solvent; (d) optionally release retarding agent(s); (e) optionally stabilizing agent(s); (f) optionally pharmaceutical excipient(s); and (g) active pharmaceutical ingredient(s) (API).

A. Surfactant

The liquid injectable compositions described herein includes a surfactant. Any suitable surfactant can be employed, in any suitable amount, provided it effectively lowers the surface tension (or interfacial tension) of the liquid injectable composition. In specific embodiments, the surfactant is a non-ionic surfactant. In additional specific embodiments, the surfactant can be present in about 5-80 wt. % of the composition.

In specific embodiments, the surfactant is selected from sorbitan esters, polyoxyethylenesorbitan ester, polyoxyethylated castor oil, hydrogenated polyoxyethylated castor oil, phospholipids, D-alpha-tocopheryl polyethylene glycol 1000 succinate (TPGS 1000), polyoxyethylene stearates, hydrophilic block polymers, glycerides, polyethylene ether, dodecyl betaine, coco amphoglycinate, cocamidopropyl betaine, and ethoxylated linear alcohol.

In specific embodiments, the surfactant includes at least one of polysorbate 80, polyoxyl 35 castor oil, polyoxyl 40 hydrogenated castor oil, lecithin, D-alpha-tocopheryl polyethylene glycol succinate 1000, and polyoxyethylated 12-hydroxystearic acid.

The liquid injectable compositions described herein includes a surfactant which forms a lyotropic liquid crystalline phase or a gel.

B. Gel Strength Enhancer

The liquid injectable compositions described herein include a gel strength enhancer. Any suitable gel strength enhancer can be employed, in any suitable amount, provided it effectively increases the strength of a gel and/or aids in the formation of a gel. In specific embodiments, the gel strength enhancer can be present in about 5-80 wt. % of the composition.

In specific embodiments, the gel strength enhancer is a lipophilic liquid and includes at least one of fatty acid, salt of fatty acid, fatty acid esters, medium chain triglycerides, glycerides, and propylene glycol derivative of medium chain triglycerides.

In specific embodiments, the gel strength enhancer includes at least one of oleic acid/ethyl oleate, sodium oleate, linoleic acid, linolenic acid dibutyl sebacate, benzyl benzoate, caprylic capric mono- & diglycerides, and glycerol tricaprylate/caprate.

C. Release Retarding Agent

The liquid injectable compositions described herein optionally include a release retarding agent. Any suitable release retarding agent can be employed, in any suitable amount, provided it effectively inhibits the release of active pharmaceutical ingredient from the composition, e.g., after it is administered to the subject and the composition forms a depot in situ. In specific embodiments, the release retarding agent can be present in about 0.01-40 wt. % of the composition.

In specific embodiments, the release retarding agent includes at least one of poly lactide co glycolide, polylactide, polyglycolide, polyethylene glycol, poly(lactide-co-caprolactone), polycaprolactone, polyethylene glycol-PLGA, glyceryl monostearate, polyglyceryl-distearate, glyceryl palmitostearate, palmitic, stearic, arachidic, behenic, and lignoceric acids and esters thereof.

D. Solvent

The liquid injectable compositions described herein include a solvent. Any suitable solvent can be employed, in any suitable amount, provided it effectively dissolves the relevant substances in the composition, in the formation of a gel. In specific embodiments, the solvent can be present in about 5-80 wt. % of the composition.

In specific embodiments, the solvent includes at least one of N-methyl-2-pyrrolidone, 2-pyrrolidone, glycofurol, dimethylacetamide, propylene glycol and benzyl alcohol.

E. Stabilizing Agent

The liquid injectable compositions described herein optionally include a stabilizing agent. Any suitable stabilizing agent can be employed, in any suitable amount, provided it effectively increases the stability of composition, including the specific compounds present therein. In specific embodiments, the stabilizing agent can be present in about 0.001-10 wt. % of the composition.

In specific embodiments, the stabilizing agent includes at least one of tocopherol, ascorbyl palmitate, butylated hydroxy anisole, and butylated hydroxy toluene, propyl gallate, hydroxypropyl betacyclodextrin and derivatives thereof.

F. Active Pharmaceutical Ingredient

The liquid injectable compositions described herein include one or more active pharmaceutical ingredients. Any suitable active pharmaceutical ingredient can be employed, in any suitable amount, provided it effectively treats the disease or disorder in the subject. The amount of active pharmaceutical ingredient employed will typically depend on the active pharmaceutical ingredient as well as the disease or disorder to be treated.

In specific embodiments, the active pharmaceutical ingredient is selected from analgesics, anti allergic drugs, anti dementia/Alzheimer drugs, anti-epileptic drugs, anti-infective drugs, antibiotics, antifungal drugs, anti-inflammatory drugs, antimalarial drugs, antineoplastic drugs, anti Parkinson's drug, anti-ulcerative drugs, cardiovascular drugs, dermatological drugs, endocrinology drugs, gastrointestinal drugs, hormones, muscle relaxants, neurologic drugs, ophthalmic drugs, psychiatric drugs, renal drugs, respiratory drugs, rheumatologic drugs, urologic drugs, and various mixtures, salts, prodrugs and co-drugs thereof.

In specific embodiments, the active pharmaceutical ingredient can include one or more antimalarial agent(s).

In specific embodiments, the active pharmaceutical ingredient can include at least one artemisinin derivative selected from arteether, artemether, artesunate, dihydroartemisinin, and artemotil & lumefantrine.

In specific embodiments, the active pharmaceutical ingredient can include at least one artemisinin derivative selected from arteether, artemether, artesunate, dihydroartemisinin, and artemotil & lumefantrine; and wherein the weight ratio of artemisinin derivative to lumefantrine is about 1:4 to about 1:8.

In specific embodiments, the active pharmaceutical ingredient can include at least one artemisinin derivative selected from arteether, artemether, artesunate, dihydroartemisinin, and artemotil & lumefantrine; and wherein the weight ratio of artemisinin derivative to lumefantrine is about 1:6.

In specific embodiments, the active pharmaceutical ingredient can include at least about 0.125 mg/Kg of at least one artemisinin derivative selected from arteether, artemether, artesunate, dihydroartemisinin, and artemotil and at least about 0.75 mg/Kg lumefantrine.

G. Pharmaceutical Excipients

The liquid injectable compositions described herein optionally include one or more pharmaceutical excipients. Any suitable pharmaceutical excipient can be employed, in any suitable amount, provided it effectively serves its intended purpose (e.g., facilitates drug absorption, reduces or increases viscosity, enhances solubility, etc.). The amount of pharmaceutical excipient employed will typically depend on the specific excipient, as well as the intended purpose. Suitable pharmaceutical excipients are disclosed, e.g., in the Handbook of Pharmaceutical Excipients, 8th Rev. Edition, American Pharmacists Association (APhA), Raymond C. Rowe (Editor) (2005).

IV. Administration of Liquid Injectable Compositions

Once formed, the liquid injectable compositions and unit dosage forms described herein are useful for the delivery of active ingredients to a mammal. Accordingly, the present invention also provides methods for delivering active ingredients to a mammal in a controlled release pattern. It has been surprisingly discovered that in specific embodiments, the injectable composition can be administered in a single dose or multiple doses which effectively treats the disease or disorder.

The liquid injectable compositions and unit dosage forms described herein can be delivered via parenteral administration, such as, for example, by intramuscular or subcutaneous routes.

V. Specific Ranges, Values and Embodiments

Specific ranges, values, and embodiments provided below are for illustration purposes only, and do not otherwise limit the scope of the disclosed subject matter, as defined by the claims.

In specific embodiments, the release retarding agent(s) is present.

In specific embodiments, the release retarding agent(s) is absent.

In specific embodiments, the stabilizing agent(s) is present.

In specific embodiments, the stabilizing agent(s) is absent.

In specific embodiments, the surfactant is present in about 5-80 wt. % of the composition.

In specific embodiments, the surfactant is present in up to about 80 wt. % of the composition.

In specific embodiments, the surfactant is present in at least about 5 wt. % of the composition.

In specific embodiments, the gel strength enhancer is present in about 5-80 wt. % of the composition.

In specific embodiments, the gel strength enhancer is present in up to about 80 wt. % of the composition.

In specific embodiments, the gel strength enhancer is present in art least about 5 wt. % of the composition.

In specific embodiments, the release retarding agent is present in about 0.01-40 wt. % of the composition.

In specific embodiments, the release retarding agent is present in up to about 40 wt. % of the composition.

In specific embodiments, the release retarding agent is present in at least about 0.01 wt. % of the composition.

In specific embodiments, the solvent is present in about 5-80 wt. % of the composition.

In specific embodiments, the solvent is present in up to about 80 wt. % of the composition.

In specific embodiments, the solvent is present in at least about 5 wt. % of the composition.

In specific embodiments, the stabilizing agent is present in about 0.001-10 wt. % of the composition.

In specific embodiments, the stabilizing agent is present in up to about 10 wt. % of the composition.

In specific embodiments, the stabilizing agent is present in art least about 0.001 wt. % of the composition.

In specific embodiments, the active pharmaceutical ingredient comprises at least one artemisinin derivative selected from arteether, artemether, artesunate, dihydroartemisinin, and artemotil & lumefantrine; and wherein the weight ratio of artemisinin derivative to lumefantrine is about 1:4 to about 1:8.

In specific embodiments, the active pharmaceutical ingredient comprises at least one artemisinin derivative selected from arteether, artemether, artesunate, dihydroartemisinin, and artemotil & lumefantrine; and wherein the weight ratio of artemisinin derivative to lumefantrine is at least about 1:4.

In specific embodiments, the active pharmaceutical ingredient comprises at least one artemisinin derivative selected from arteether, artemether, artesunate, dihydroartemisinin, and artemotil & lumefantrine; and wherein the weight ratio of artemisinin derivative to lumefantrine is up to about 1:8.

In specific embodiments, the active pharmaceutical ingredient comprises at least one artemisinin derivative selected from arteether, artemether, artesunate, dihydroartemisinin, and artemotil lumefantrine; and wherein the weight ratio of artemisinin derivative to lumefantrine is about 1:6.

In specific embodiments, the composition is used for the treatment of malaria by administering a single or multiple dose of at least about 0.125 mg/Kg of at least one artemisinin derivative selected from arteether, artemether, artesunate, dihydroartemisinin, and artemotil and at least about 0.75/Kg lumefantrine.

In specific embodiments, the composition is used for the treatment of malaria by administering a single dose of up to about 1.0 mg/Kg of at least one artemisinin derivative selected from arteether, artemether, artesunate, dihydroartemisinin, and artemotil; and up to about 6.0 mg/Kg lumefantrine.

In specific embodiments, the unit dosage form contains about 400-4000 mcL of the composition.

In specific embodiments, the unit dosage form contains up to about 4000 mcL of the composition.

In specific embodiments, the unit dosage form comprises 7.5 to 30 mg arteether or 7.5 to 30 mg of Artemether.

In specific embodiments, the unit dosage form comprises about 45-180 mg lumefantrine.

In specific embodiments, the unit dosage form comprises about 100-800 mcL oleic acid.

In specific embodiments, the unit dosage form comprises about 100-1200 mcL polyoxyethylene sorbitan ester.

In specific embodiments, the unit dosage form comprises about 100-1000 mcL benzyl benzoate.

In specific embodiments, the unit dosage form comprises about 100-1200 mcL N-methyl-2-pyrrolidone.

In specific embodiments, the unit dosage form comprises about 5-40 mg Poly lactide/glycolide; 50:50 (PLGA).

In specific embodiments, the unit dosage form does not contain di butyl sebacate, 2-pyrrolidone polyglyceryldistearate (PGDS), or any combination thereof.

The composition of the present invention may comprise less than about 2.5 wt. % moisture, preferably less than about 1% moisture and more preferably 0.5% moisture.

VI. Enumerated Embodiments

Specific enumerated embodiments [1] to [37] provided below are for illustration purposes only, and do not otherwise limit the scope of the disclosed subject matter, as defined by the claims. These enumerated embodiments encompass all combinations, sub-combinations, and multiply referenced (e.g., multiply dependent) combinations described therein.

[1.] The present invention provides for a liquid injectable composition comprising:
(a) at least one surfactant;
(b) at least one gel strength enhancer;
(c) at least one solvent;
(d) optionally release retarding agent(s);
(e) optionally stabilizing agent(s);
(f) optionally pharmaceutical excipient(s); and
(g) active pharmaceutical ingredient(s) (API).

[2.] The present invention also provides for the composition of embodiment [1], wherein the surfactant is present in about 5-80 wt. % of the composition.

[3.] The present invention also provides for the composition of any one of embodiments [1]-[2], wherein the surfactant is non-ionic.

[4.] The present invention also provides for the composition of any one of embodiments [1]-[3], wherein the surfactant is selected from sorbitan esters, polyoxyethylene sorbitan ester, polyoxyethylated castor oil, hydrogenated polyoxyethylated castor oil, phospholipids, D-alpha-tocopheryl polyethylene glycol 1000 succinate (TPGS 1000), polyoxyethylene stearates, hydrophilic block polymers, glycerides, polyethylene ether, dodecyl betaine, coco amphoglycinate, cocamidopropyl betaine, and ethoxylated linear alcohol.

[5.] The present invention also provides for the composition of any one of embodiments [1]-[4], wherein the surfactant comprises at least one of polysorbate 80, -polyoxyl 35 castor oil, polyoxyl 40 hydrogenated castor oil, lecithin, D-alpha-tocopheryl polyethylene glycol succinate 1000, and polyoxyethylated 12-hydroxystearic acid.

[6.] The present invention also provides for the composition of any one of embodiments [1]-[5], wherein the surfactant forms a lyotropic liquid crystalline phase or a gel.

[7.] The present invention also provides for the composition of any one of embodiments [1]-[6], wherein the gel strength enhancer is present in about 5-80 wt. % of the composition.

[8.] The present invention also provides for the composition of any one of embodiments [1]-[7], wherein the gel strength enhancer is a lipophilic liquid and comprises at least one of fatty acid, salt of fatty acid, fatty acid esters, medium chain triglycerides, glycerides, and propylene glycol derivative of medium chain triglycerides.

[9.] The present invention also provides for the composition of any one of embodiments [1]-[8], wherein the gel strength enhancer comprises at least one of oleic acid/ethyl oleate, sodium oleate, linoleic acid, linolenic acid dibutyl sebacate, benzyl benzoate, caprylic capric mono- & diglycerides, and glyceroltricaprylate/caprate.

[10.] The present invention also provides for the composition of any one of embodiments [1]-[9], wherein the release retarding agent is present in about 0.01-40 wt. % of the composition.

[11.] The present invention also provides for the composition of any one of embodiments [1]-[10], wherein the release retarding agent comprises at least one of a polymer and lipid.

[12.] The present invention also provides for the composition of any one of embodiments [1]-[11], wherein the release retarding agent comprises at least one of poly (lactide-co-glycolide), polylactide, polyglycolide, polyethylene glycol, poly(lactide-co-caprolactone), polycaprolactone, polyethylene glycol-PLGA, glyceryl monostearate, polyglyceryl-distearate, glyceryl palmitostearate, palmitic, stearic, arachidic, behenic, and lignoceric acids and esters thereof.

[13.] The present invention also provides for the composition of any one of embodiments [1]-[12], wherein the solvent is present in about 5-80 wt. % of the composition.

[14.] The present invention also provides for the composition of any one of embodiments [1]-[13], wherein the solvent comprises at least one of N-methyl-2-pyrrolidone, 2-pyrrolidone, glycofurol, dimethylacetamide, propylene glycol and benzyl alcohol.

[15.] The present invention also provides for the composition of any one of embodiments [1]-[14], containing less than about 1 wt. % moisture.

[16.] The present invention also provides for the composition of any one of embodiments [1]-[15], wherein the stabilizing agent is present in about 0.001-10 wt. % of the composition.

[17.] The present invention also provides for the composition of any one of embodiments [1]-[16], wherein the stabilizing agent comprises at least one of tocopherol, ascorbyl palmitate, butylated hydroxy anisole, and butylated hydroxy toluene, propyl gallate, hydroxypropyl betacyclodextrin and derivatives thereof.

[18.] The present invention also provides for the composition of any one of embodiments [1]-[17], where the active pharmaceutical ingredient is selected from analgesics, anti allergic drugs, anti dementia/Alzheimer drugs, anti-epileptic drugs, anti-infective drugs, antibiotics, antifungal drugs, anti-inflammatory drugs, antimalarial drugs, antineoplastic drugs, anti Parkinson's drug, anti-ulcerative drugs, cardiovascular drugs, dermatological drugs, endocrinology drugs, gastrointestinal drugs, hormones, muscle relaxants, neurologic drugs, ophthalmic drugs, psychiatric drugs, renal drugs, respiratory drugs, rheumatologic drugs, urologic drugs, and various mixtures, salts, prodrugs and co-drugs thereof.

[19.] The present invention also provides for the composition of any one of embodiments [1]-[18], wherein the active pharmaceutical ingredient comprises antimalarial agent(s).

[20.] The present invention also provides for the composition of embodiment [19], wherein the active pharmaceutical ingredient comprises at least one artemisinin derivative selected from arteether, artemether, artesunate, dihydroartemisinin, and artemotil & lumefantrine.

[21.] The present invention also provides for the composition of embodiment [19], wherein the active pharmaceutical ingredient comprises at least one artemisinin derivative selected from arteether, artemether, artesunate, dihydroartemisinin, and artemotil & lumefantrine; and wherein the weight ratio of artemisinin derivative to lumefantrine is about 1:4 to about 1:8.

[22.] The present invention also provides for the composition of embodiment [19], wherein the active pharmaceutical ingredient comprises at least one artemisinin derivative selected from arteether, artemether, artesunate, dihydroartemisinin, and artemotil & lumefantrine; and wherein the weight ratio of artemisinin derivative to lumefantrine is about 1:6.

[23.] The present invention also provides for the composition of any one of embodiments [1]-[22], for treatment of malaria by administering a single dose of at least about 0.125 mg/Kg of at least one artemisinin derivative selected from arteether, artemether, artesunate, dihydroartemisinin, and artemotil and at least about 0.75 mg/Kg lumefantrine.

[24.] The present invention also provides for the composition of embodiment [23], formulated as a unit dosage form for single or multiple dose therapy for prevention or treatment of malaria.

[25.] The present invention also provides for the composition of any one of embodiments [1]-[24], which is at least one of (a)-(k):
  (a) liquid injectable dosage form;
  (b) water-free self microemulsifying drug delivery system (SMEDDS), which on contact with water forms a liquid crystalline phase;
  (c) liquid injectable dosage form, capable of forming a depot in situ;
  (d) liquid injectable dosage form, capable of forming a depot in situ, which releases the one or more active pharmaceutical ingredients over a period of time;
  (e) liquid injectable dosage form, capable of forming a gel in situ in contact with aqueous fluids;
  (f) liquid injectable dosage form, capable of forming a gel in situ, in contact with aqueous fluid and releases the one or more active pharmaceutical ingredients over a period of time;
  (g) controlled release liquid injectable dosage form;
  (h) modified release liquid injectable dosage form;
  (i) sustained release liquid injectable dosage form;
  (j) extended release liquid injectable dosage form; and
  (k) liquid injectable dosage form, capable of forming a depot in situ with a reduced burst effect.

[26.] The present invention also provides for the composition of embodiment [25], wherein the liquid injectable dosage form is a ready to inject dosage form in vials or prefilled syringe.

[27.] The present invention also provides for the composition of any one of embodiments [1]-[26], which is a unit dosage form of about 400-4,000 mcL, the composition comprising arteether and lumefantrine, or artemether and lumefantrine preferably a unit dosage form of about 400-4, 000 mcL, the composition comprising
  (i) about 7.5-30 mg arteether or arteether/artemether
  (ii) about 45-180 mg lumefantrine, and one or more excipients selected from
About 100-800 mcL oleic acid or about 200-1200 mcL polyoxyethylene sorbitan ester or about 100-1000 mcL benzyl benzoate or about 100-1200 mcL N-methyl pyrrolidone, and about 5-40 mg Poly lactide/glycolide; 50:50 (PLGA).

[28.] The present invention also provides for the composition of embodiment [1 to 27], will not compose di butyl sebacate, 2-pyrrolidone polyglyceryldistearate (PGDS), or any combination thereof.

[29] The present invention also provides for the composition of embodiment [1 to 28] wherein the gel strength of the composition is at least 0.07 mJ.

[30.] The present invention also provides for the composition of embodiment [27], wherein the active pharmaceutical ingredient comprises antimalarial agents and the composition is formulated as a unit dosage form for single or multiple dose therapy for the treatment of malaria.

[31.] The present invention also provides for the composition of any one of embodiments [1]-[30], used to prepare a medicament.

[32.] The present invention also provides for a method of treating a subject suffering from a disease or disorder ameliorated by one or more of the active pharmaceutical ingredients, the method comprising administering the composition of any one of the above embodiments (e.g., any one of embodiments [1]-[31]), in an amount and for a period of time sufficient to treat the subject.

[33.] The present invention also provides for the method of embodiment [32], wherein the subject is a human.

[34.] The present invention also provides for the method of any one of embodiments [31]-[33], wherein the disease or disorder is malaria.

[35.] The present invention also provides for the method of any one of embodiments [31]-[34], wherein composition is administered in a single or multiple dose which effectively treats the disease or disorder.

[36.] The present invention also provides for the method of any one of embodiments [31]-[35], wherein the administration is intramuscular or subcutaneous.

[37.] The present invention also provides for the method of any one of embodiments [31]-[36], wherein the active pharmaceutical ingredient comprises an antimalarial and the composition is formulated as a unit dosage form for single or multiple dose therapy, equal to or greater than 0.75 mg/Kg of lumefantrine and equal to or greater than 0.125 mg/Kg of artemisinin derivative for the treatment of malaria.

[38.] The present invention also provides for the method of any one of embodiments [31]-[36], wherein the active pharmaceutical ingredient comprises an antimalarial and the composition is formulated as a unit dosage form for single or multiple dose therapy, equal to or greater than 0.125 mg/Kg of artemisinin derivative and 0.75 mg/Kg of lumefantrine, for the treatment of malaria caused by *P. falciparum*.

VII. Examples

Example 1: Screening of Non Ionic Surfactants and Gel Strength Enhancers for Preparation of Gelling Lipid Phase Method for Qualitative Evaluation of Gel Formation Various non ionic surfactants and potential gel strength enhancers were mixed together with or without addition of solvent and evaluated to check their capability of gel formation as given below:

Method 1: For example 1.1 a-c, example 1.2a-d, example 1.3 a-d and example 1.4 a-d, 30 mcL of water was taken in micro centrifuge tube, 60 mcL of the composition was added to it and kept aside. After 30 seconds the mixture was stirred and after 60 seconds the micro centrifuge tube was inverted to check for gel formation.

Method 2: For example 1.5 a-d, example 1.6 a-d and example 1.7 a-d; 60 mcL of solution was added into a petri plate containing about 10-15 ml water at room temperature. Strength of the formed gel was evaluated after 30 seconds qualitatively by disturbing gel matrix using 200 mcL micropipette tip. All observations given in Table 1 and recorded based on the scores allotted as given in Table 2.

TABLE 1

Qualitative gel formation experiment
Example 1

| Example No | Non ionic surfactant Name | Quantity | Gel strength enhancer Name | Quantity | Solvent Name | Quantity | Gel formation score |
|---|---|---|---|---|---|---|---|
| 1.1a | Polyoxyethylene sorbitanmonooleate (Polysorbate 80) | 50% v/v | Benzyl Benzoate | 50% v/v | NA | | ++ |
| 1.1b | Polyoxyethylenesorbitanmonooleate (Polysorbate 80) | 50% v/v | Dibutylsebacate | 50% v/v | NA | | +++++ |
| 1.1c | Polyoxyethylenesorbitanmonooleate (Polysorbate 80) | 50% v/v | Oleic acid | 50% v/v | NA | | ++ |
| 1.2a | Polyoxyethylenesorbitanmonolaurate (Polysorbate 20) | 50% v/v | Dibutylsebacate | 50% v/v | NA | | ++ |
| 1.2b | Polyoxyethylenesorbitanmonolaurate (Polysorbate 20) | 50% v/v | Benzyl Benzoate | 50% v/v | NA | | ++ |
| 1.2c | Polyoxyethylenesorbitanmonolaurate (Polysorbate 20) | 50% v/v | Mono-diglyceride of medium chain fatty acids | 50% v/v | NA | | ++ |
| 1.2d | Polyoxyethylenesorbitanmonolaurate (Polysorbate 20) | 50% v/v | Oleic acid | 50% v/v | NA | | + |
| 1.3a | Polyoxyl 35 castor oil | 50% v/v | Dibutylsebacate | 50% v/v | NA | | ++++ |
| 1.3b | Polyoxyl 35 castor oil | 50% v/v | Benzyl Benzoate | 50% v/v | NA | | ++ |
| 1.3c | Polyoxyl 35 castor oil | 50% v/v | Mono-diglyceride of medium chain fatty acids | 50% v/v | NA | | + |
| 1.3d | Polyoxyl 35 castor oil | 50% v/v | Oleic acid | 50% v/v | NA | | ++ |
| 1.4a | Sorbitanmonooleate (Span 80) | 50% v/v | Dibutylsebacate | 50% v/v | NA | | − |
| 1.4b | Sorbitanmonooleate (Span 80) | 50% v/v | Benzyl Benzoate | 50% v/v | NA | | − |
| 1.4c | Sorbitanmonooleate (Span 80) | 50% v/v | Mono-diglyceride of medium chain fatty acids | 50% v/v | NA | | − |
| 1.4d | Sorbitanmonooleate (Span 80) | 50% v/v | Oleic acid | 50% v/v | NA | | + |
| 1.5a | D-alpha-tocopheryl polyethylene glycol succinate 1000 (TPGS 1000) | 50 mg | Dibutylsebacate | 100 mcL | NMP | 100 mcL | ++++ |
| 1.5b | D-alpha-tocopheryl polyethylene glycol succinate 1000 (TPGS 1000) | 50 mg | Mono-diglyceride of medium chain fatty acids | 100 mcL | NMP | 100 mcL | +++ |
| 1.5c | D-alpha-tocopheryl polyethylene glycol succinate 1000 (TPGS 1000) | 50 mg | Oleic acid | 100 mcL | NMP | 100 mcL | +++ |
| 1.5d | D-alpha-tocopheryl polyethylene glycol succinate 1000 (TPGS 1000) | 50 mg | Benzyl Benzoate | 100 mcL | NMP | 100 mcL | − |

TABLE 1-continued

Qualitative gel formation experiment
Example 1

| Example No | Non ionic surfactant Name | Quantity | Gel strength enhancer Name | Quantity | Solvent Name | Quantity | Gel formation score |
|---|---|---|---|---|---|---|---|
| 1.6a | Polyoxyl40 hydrogenated castor oil | 70 mg | Dibutylsebacate | 100 mcL | NA | | ++++ |
| 1.6b | Polyoxyl40 hydrogenated castor oil | 70 mg | Mono-diglyceride of medium chain fatty acids | 100 mcL | NA | | +++ |
| 1.6c | Polyoxyl40 hydrogenated castor oil | 70 mg | Oleic acid | 100 mcL | NA | | + |
| 1.6d | Polyoxyl40 hydrogenated castor oil | 70 mg | Benzyl Benzoate | 100 mcL | NA | | ++ |
| 1.7a | Polyoxyethylated 12-hydroxystearic acid | 100 mg | Dibutylsebacate | 150 mcL | NA | | +++++ |
| 1.7b | Polyoxyethylated 12-hydroxystearic acid | 100 mg | Mono-diglyceride of medium chain fatty acids | 150 mcL | NA | | ++ |
| 1.7c | Polyoxyethylated 12-hydroxystearic acid | 100 mg | Oleic acid | 150 mcL | NA | | +++ |
| 1.7d | Polyoxyethylated 12-hydroxystearic acid | 100 mg | Benzyl Benzoate | 150 mcL | NA | | + |

NA: Not added

TABLE 2

Qualitative gel formation assessment score:

| Score | Qualitative Gel formation |
|---|---|
| − | No gel formation |
| + | Very poor |
| ++ | Poor |
| +++ | Fair |
| ++++ | Good |
| +++++ | Excellent |

Dibutyl sebacate, oleic acid and mono-diglyceride of medium chain fatty acids were found to exhibit good gel formation ability with most of the surfactants whereas benzyl benzoate was found to provide gel formation with some of the surfactants. The surfactants—polysorbate 80, Polyoxyl 35 castor oil, Polyoxyl 40 hydrogenated castor oil, TPGS 1000 and Polyoxyethylated 12-hydroxystearic acid are found to have stronger gel formation ability than Span 80 and Polysorbate 20.

Example 2: Compositions with Lipid Phase and Solvents

Quantitative Evaluation of Gel Strength Using Texture Analyzer:

Method: Gel strength (GS) was analyzed on Brookfield, CTE3, 100 g set on a compression mode, using TA 10 (12.7 mm diameter cylindrical) probe. Samples were prepared by addition of PBS (pH 7.4) to example 2.1-2.15 followed by stirring. Samples were kept for 1 h equilibration before analyzing the gel strength. Gel strength was measured in terms of hardness work cycle 1 (mJ) with zero trigger load and 10 mm penetration height. Non ionic surfactants, gel strength enhancers and solvents were mixed in the proportion mentioned in Table 3 and analyzed for gel strength evaluation. A gel strength value ≥0.07 mJ is considered acceptable based on physical observation.

TABLE 3

Composition and quantitative evaluation of gel strength of example 2:
Example 2

| Ingredients (mcL) | 2.1 | 2.2 | 2.3 | 2.4 | 2.5 | 2.6 | 2.7 | 2.8 | 2.9 |
|---|---|---|---|---|---|---|---|---|---|
| Oleic Acid | 0 | 200 | 0 | 200 | 0 | 200 | 400 | 0 | 100 |
| Mono-diglyceride of medium chain fatty acids | 0 | 0 | 0 | 0 | 0 | 0 | 0 | 0 | 0 |
| Dibutyl sebacate | 0 | 0 | 200 | 0 | 400 | 200 | 0 | 200 | 0 |
| Benzyl Benzoate | 0 | 0 | 0 | 0 | 0 | 0 | 0 | 0 | 100 |
| Polysorbate 80 | 400 | 0 | 0 | 400 | 400 | 400 | 400 | 400 | 400 |
| N Methyl 2 Pyrrolidone | 200 | 200 | 200 | 200 | 200 | 200 | 200 | 200 | 200 |
| Total | 600 | 400 | 400 | 800 | 1000 | 1000 | 1000 | 800 | 800 |
| Gel Strength (mJ) Avg ± SD (n = 3) | 0.067 ± 0.01 | 0.043 ± 0.01 | 0.05 | 0.21 ± 0.03 | 0.117 ± 0.01 | 0.13 ± 0.01 | 0.07 | 0.10 ± 0.01 | 0.15 ± 0.02 |

TABLE 3-continued

Composition and quantitative evaluation of gel strength of example 2:
Example 2

| Ingredients (mcL) | 2.10 | 2.11 | 2.12 | 2.13 | 2.14 | 2.15 |
|---|---|---|---|---|---|---|
| Oleic Acid | 200 | 0 | 0 | 0 | 0 | 200 |
| Mono-diglyceride of medium chain fatty acids | 0 | 0 | 0 | 400 | 200 | 200 |
| Dibutyl sebacate | 0 | 0 | 0 | 0 | 0 | 0 |
| Benzyl Benzoate | 200 | 200 | 400 | 0 | 0 | 0 |
| Polysorbate 80 | 400 | 400 | 400 | 400 | 400 | 400 |
| N Methyl 2 Pyrrolidone | 200 | 200 | 200 | 200 | 200 | 200 |
| Total | 1000 | 800 | 1000 | 1000 | 800 | 1000 |
| Gel Strength (mJ) Avg ± SD (n = 3) | 0.11 ± 0.01 | 0.06 | 0.05 ± 0.01 | 0.06 | 0.05 ± 0.005 | 0.06 |

Gel strength ≥ 0.07 mJ was considered as good gel strength

Non ionic surfactant (Polysorbate 80) in combination with solvent NMP did not exhibit acceptable gel strength (example 2.1). Similarly acceptable gel strength was not observed with oleic acid or dibutyl sebacate or as gel strength enhancer alone (example 2.2 & 2.3) in presence of solvent NMP. However when dibutyl sebacate or oleic acid gel strength enhancers (example 2.4, 2.5, 2.7 and 2.8) or mixture of dibutyl sebacate or oleic acid as gel strength enhancer (example 2.6) was combined with non ionic surfactant i.e. Polysorbate 80 in presence of NMP, gel strength was found to increase. Thus synergy of using combination of non ionic surfactant and gel strength enhancer in gel formation is established. Example 2.9 and 2.10 exhibited gel strength enhancing property of benzyl benzoate in combination with oleic acid however benzyl benzoate alone failed to impart sufficient gel strength (Example no 2.11 and example no 2.12). Mono-diglyceride of medium chain fatty acids showed poor gel strength enhancing property as compared to oleic acid, benzyl benzoate and DBS. (Example no. 2.13, 2.14 and 2.15)

Example 3: Anti-Malarial Injectable Composition

Example 3 is an intramuscular controlled release injection with combination of two antimalarial drugs arteether (20 mg) and lumefantrine (120 mg) indicated as a single dose therapy for complicated malaria caused due to *P falciparum*. This example is designed to release drugs over a period of time and it also obviates the need to administer artemisinin based oral combination therapy (ACT) and hence serving as a single dose patient friendly therapy.

TABLE 4

Compositions of example 3.1, example 3.2, example 3.3 and example 3.4:
Example 3

| Ingredients | 3.1 | 3.2 | 3.3 | 3.4 |
|---|---|---|---|---|
| Arteether (mg) | 20 | 20 | 20 | 20 |
| Lumefantrine (mg) | 120 | 120 | 120 | 120 |
| Oleic Acid (mcL) | 200 | 200 | 200 | 200 |
| Di butyl Sebacate (DBS) (mcL) | 200 | 200 | 200 | 200 |
| Polysorbate 80 (mcL) | 400 | 400 | 400 | 400 |
| N-Methyl Pyrrolidone (NMP) (mcL) | 200 | 200 | — | — |
| 2-Pyrrolidone (SoluphorP) (mcL) | — | — | 200 | 200 |
| Poly lactide/glycolide; 50:50 (PLGA) (mg) | — | 10 | — | — |
| Polyglyceryldistearate (PGDS)(mg) | — | — | — | 10 |
| Total (mcL) | 1000 | 1000 | 1000 | 1000 |

Preparation:

Oleic acid, DBS and Polysorbate 80 were mixed together. PLGA was dissolved in NMP while PGDS was dissolved in soluphor P and added to the mixture of the oil phase and mixed well. Lumefantrine and arteether were then dissolved in the above solutions one by one, and the solution was mixed well.

Examples were Evaluated for Following Tests

1: Sol to Gel Conversion Study:

To evaluate sol to gel conversion, the viscosity of example 3.2 and example 3.4 was determined using cone and plate programmable rheometer (Physica MCR101, Germany) connected to a digital thermostatically controlled circulating water bath (Polyscience, Model 9101, USA) with spindle CP35-2-SN20784 (d=0.147 mm). The shear rate applied was increased from 0 to 500 seconds$^{-1}$ for a time period of one minute and decreased back to 0 seconds$^{-1}$ within the next one minute. Measurements were recorded after equilibration for 5 mm following loading at a constant temperature of 20° C.

TABLE 5

Sol to gel conversion study:
Example 3

| Viscosity(cps) | 3.2 | 3.4 |
|---|---|---|
| Before water addition | 50 ± 0.0175 | 31 ± 0.015 |
| After water addition | 475 ± 0.43 | 471 ± 0.155 |
| Viscosity enhancement | 9-Fold enhancement | 15-Fold enhancement |

Significant increase in viscosity of both example 3.2 and example 3.4 after water addition indicated conversion of solution to gel phase.

2: Polarization Optical Microscopy (POM)

One drop of water and one drop of example 3.1, example 3.2, example 3.3, and example 3.4 were placed on a microscope slide in close proximity to each other. A clean needle was used to mix the water droplets with the solutions of examples 3.1, example 3.2, example 3.3, and example 3.4 and the water content gradually increased. The phase transition of formulations to form viscous and liquid crystalline phase (gel) was continuously monitored under polarized light microscope (Leica DM EP, USA).

Figure 1:
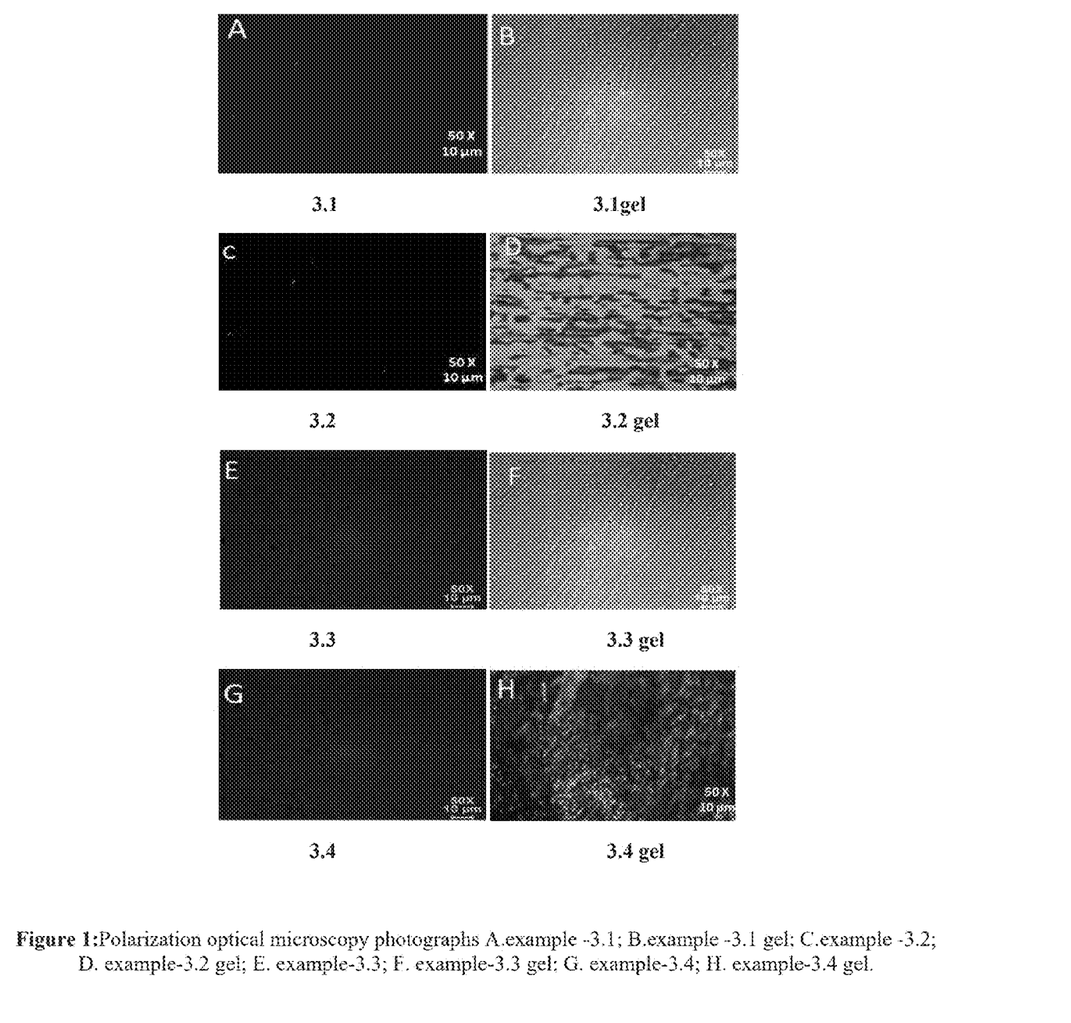
FIG. 1 are photographs depicting Polarization optical microscopy analysis of Example 3 compositions when prepared (A, C, E and G) and post addition of water to the Example 3 compositions (B, D, F and H respectively).

POM enables visualization of birefringence exhibited by liquid crystalline phases both lamellar and hexagonal. Similarly, POM photomicrographs (FIG. 1) revealed that all compounds appeared as dark background indicating isotropic nature. However following addition of water, all examples exhibited birefringence confirming the formation of liquid crystalline phase. The photomicrographs (FIGS. 1D & H) depicted that inclusion of polymer and lipid enabled formation of 3 dimensional network structures compared to example 3.1 and example 3.3.

3: Effect of PLGA or PGDS on Gel Strength:

Gel strength was evaluated using CT3 (Brookfield Engineering Labs Inc., USA) with compression mode, using cylindrical probe of 7.6 cm having test speed of 1 mm/sec with 5-10 g trigger load. 50 g sample was prepared by addition of 50% v/w water to examples 3.1, example 3.2, example 3.3, and example 3.4.

TABLE 6

Comparative gel strength with/without PLGA/PGDS Example 3

| Gel Strength | 3.1 | 3.2 | 3.3 | 3.4 |
|---|---|---|---|---|
| Gel strength (mJ) | 0.258 ± 0.11 | 0.9 ± 0.12 | 0.112 ± 0.2 | 0.75 ± 0.2 |
| Gel strength Enhancement | | 3-fold enhancement with addition of PLGA | | 6-fold enhancement with addition of PGDS |

The increase in gel strength after addition of release retardants confirmed formation of 3-D matrix structure.

Figure 2:
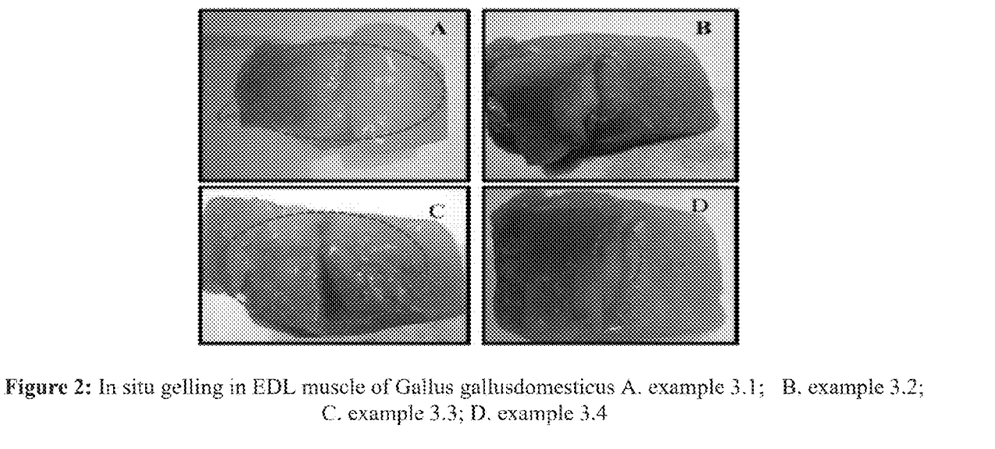
FIG. 2 are photographs depicting in situ gelling of Examples 3.1 to 3.4 in EDL muscle of *Gallus gallus domesticus*.

4: In Situ Gelling in Extensor Digitorum Longns Muscle (EDL) of *Gallus gallus Domesticus*:

Example 3.1, example 3.2, example 3.3, and example 3.4 with coumarin were prepared and injected into EDL muscle of *Gallus gallus domesticus* and gel formation observed visually. Example 3.1 and example 3.3 diffused into the muscle and spread out within 30 min, the inclusion of PLGA (example 3.2) and PGDS (example 3.4) formed stiff gel which remained intact at the site of injection over 3 h as seen in FIG. 2.

5: Ex Vivo Release Study in Extensor Digitorumlongus Muscle of *G. domesticus*

Arteether and Lumefantrine solution and example 3.1, example 3.2, example 3.3 and example 3.4 equivalent to 5 mg of arteether and 30 mg of lumefantrine were injected to a depth of 0.75 mm into the muscle (1.6 mg) using a marked 21G needle. The muscle was placed in the vessel of an organ bath with 50 mL of PBS (pH 7.4) comprising 0.5% Polysorbate 80 as the dissolution medium. The medium was maintained at 37±0.5° C. and air was bubbled at constant rate of 10 bubbles/sec to provide agitation. At 0.5, 1, 2, 4, 8, 12, 24, 48, and 72 h samples (1 mL) were withdrawn and replaced with fresh PBS to maintain sink conditions. The samples were analyzed for arteether and lumefantrine at 254 nm and 234 nm, respectively by UV spectrophotometer.

Figure 3:
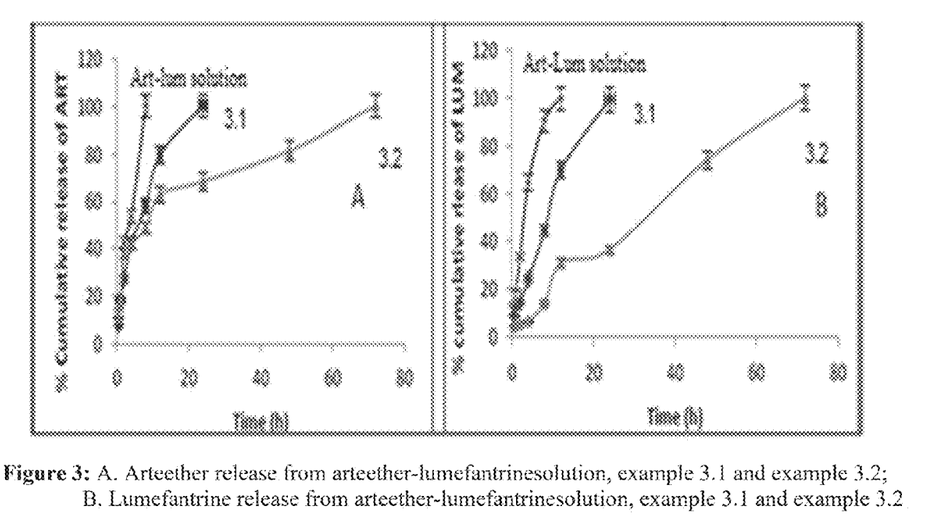
FIG. 3 are graphical representations of Arteether and Lumefantrine release from Examples 3.1 and 3.2.
Figure 4:
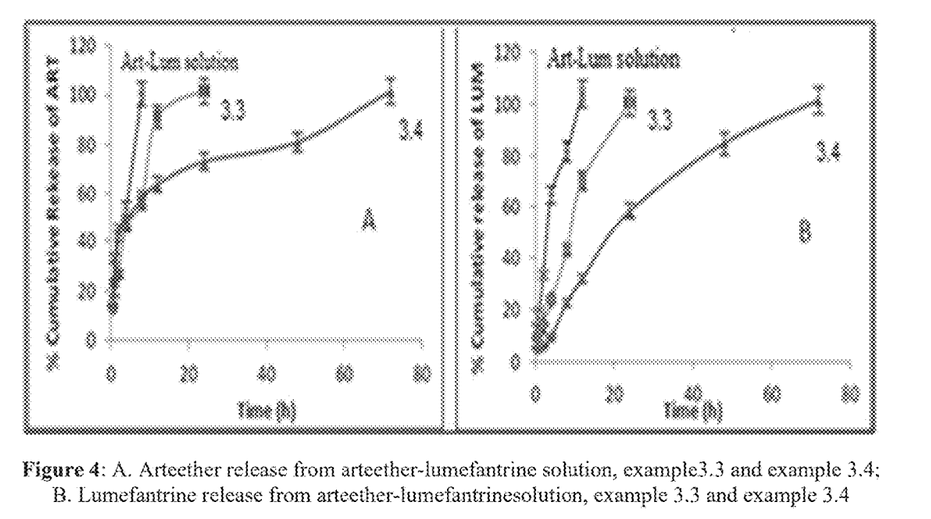
FIG. 4 are graphical representations of Arteether and Lumefantrine release from Examples 3.3 and 3.4.

Arteether release was faster than lumefantrine. Further example 3.2 and example 3.4 revealed controlled release over 3 days of arteether and lumefantrine. (FIGS. 3 and 4)

6 Antimalarial Efficacy Study: Clinical Simulation Study:

Method: The efficacy of the treatment was evaluated in a clinical simulation study, where the parasitemia was allowed to rise to 10-15% before commencement of treatment. Swiss male mice (30±5 g) were infected with donor blood infected with *P. berghei* ANKA. Arteether marketed product, Example 3.2 at $1/20^{th}$, $1/40^{th}$, $1/80^{th}$ of the therapeutic dose were administered intramuscularly once parasitemia count rose to 10-15%. Percentage parasitemia count and survival was evaluated at predetermined time from injection to assess the efficacy and safety.

TABLE 7

Clinical simulation study protocol for Example 3.2 (1/20, 1/40 and 1/80$^{th}$ therapeutic dose) and for marketed product: Example 3.2

| No | Groups | Days | Dose of Arteether | Dose of Lumefantrine | P-value against marketed product |
|---|---|---|---|---|---|
| 1 | Control | — | — | — | — |
| 2 | Example 3.2 (1/20 dose) | Single dose on day zero | 0.16 mg/kg (1/20) | 0.96 mg/kg (1/20) | 0.0005 |
| 3 | Example 3.2 (1/40 dose) | Single dose on day zero | 0.08 mg/kg (1/40) | 0.48 mg/kg (1/40) | 0.0005 |
| 4 | Example 3.2 (1/80 dose) | Single dose on day zero | 0.04 mg/kg (1/80) | 0.24 mg/kg (1/80) | 0.34 |
| 5 | Marketed product E-Mal ® | Three doses on day zero, one, two | 3.2 mg/kg BW | — | — |

Figure 5:
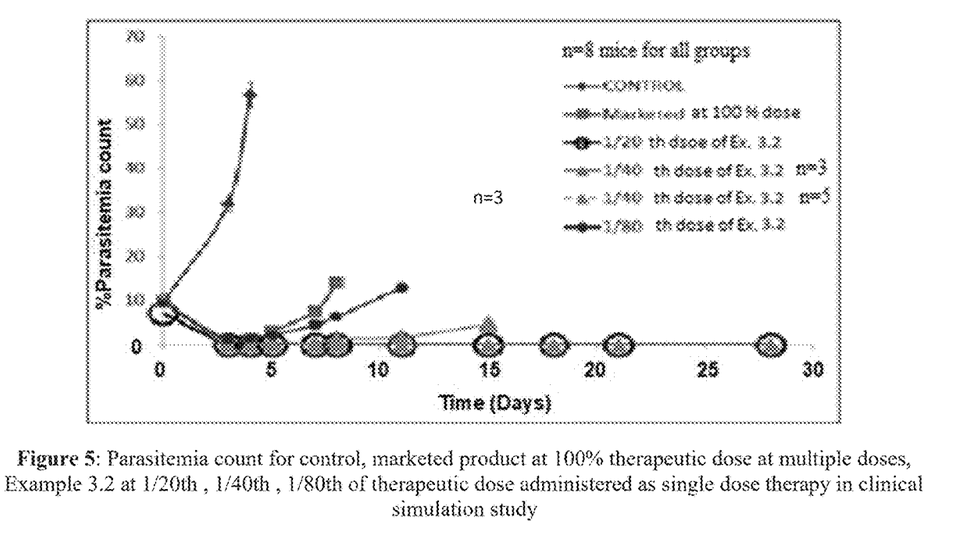
FIG. 5 is a graphical representation of parasitemia count when composition of control, marketed product at 100% therapeutic dose at multiple doses and Example 3.2 at 1/20, 1/40 and 1/80 of therapeutic dose administered as single dose in clinical simulation study.
Figure 6:
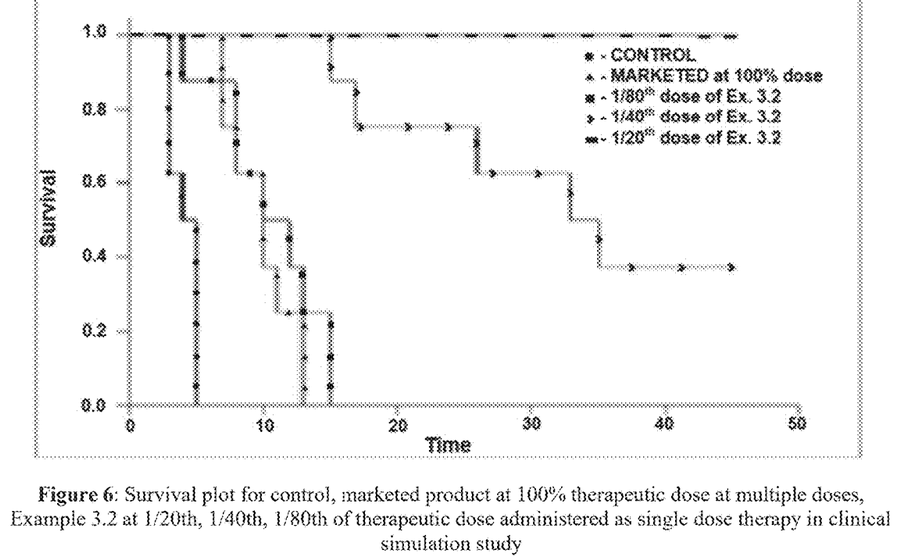
FIG. 6 shows a survival plot when composition of control, marketed product at 100% therapeutic dose at multiple doses and Example 3.2 at 1/20, 1/40 and 1/80 of therapeutic dose administered as single dose in clinical simulation study.

Example 3.2 with $1/20^{th}$ of therapeutic dose resulted in complete clearance of parasitemia with no recrudescence (FIG. 5) and with 100% survival of experimental mice for 45 days (FIG. 6) in contrast to marketed arteether injection for which recrudescence was observed after 5 days and 100% mortality of experimental mice was noted within 15 days. The clinical simulation study proved that example 3.2 is effective at $1/20^{th}$ of therapeutic dose as a single dose therapy while at lower doses it showed recrudescence.

TABLE 8

Compositions of example 3.5, example 3.6, example 3.7, example 3.8, example 3.9, example 3.10, example 3.11 and example 3.12:

| Ingredients | 3.5 | 3.6 | 3.7 | 3.8 | 3.9 | 3.10 | 3.11 | 3.12 |
|---|---|---|---|---|---|---|---|---|
| Arteether (mg) | 10 | 10 | 10 | 10 | 10 | 10 | — | — |
| Artemether (mg) | — | — | — | — | — | — | 10 | 10 |
| Lumefantrine (mg) | 60 | 60 | 60 | 60 | 60 | 60 | 60 | 60 |
| Oleic Acid (mcL) | 200 | 250 | 200 | 200 | 200 | 200 | 200 | 200 |
| Di butyl Sebacate (mcL) | 200 | — | — | — | — | — | 200 | — |
| Benzyl Benzoate (mcL) | — | — | — | 200 | 200 | — | — | — |
| Polysorbate 80 (mcL) | 400 | 450 | 300 | 400 | 300 | — | 400 | 300 |
| N-Methyl Pyrrolidone (mcL) | 200 | 300 | 300 | 200 | 300 | 200 | 200 | 300 |
| Poly lactide/glycolide; 50:50 (PLGA) (mg) | 10 | 10 | 10 | 10 | 10 | 10 | 10 | — |
| Total (mcL) | 1000 | 1000 | 800 | 1000 | 1000 | 400 | 1000 | 800 |

PLGA and Arteether/artemether were dissolved in NMP. Lumefantrine was dissolved in oleic acid. PLGA solution was then added to lumefantrine-oleic acid solution and mixed. Then to above mixture dibutylsebacate/benzyl benzoate and then polysorbate 80 was added and mixed well.

Examples were Evaluated for the Tests Indicated Below

1: Evaluation of Gel Strength:

Gel strength was analyzed on Brookfield, CT3, 100 g set on a compression mode, using TA 10 (12.7 mm diameter cylindrical) probe. Samples were prepared by addition of PBS (pH 7.4) to example 3.5, example 3.6, example 3.7 and example 3.8, example 3.11, example 3.12 followed by stirring. Samples were kept for 1 h equilibration before analyzing the gel strength. Gel strength was measured in terms of hardness work cycle 1 (mJ) with zero trigger load and 10 mm penetration height.

TABLE 9

Gel strengths of example 3.5, example 3.6, example 3.7, example 3.8, example 3.11 and example 3.12:
Example 3

| Example | Gel strength (hardness work in mJ) |
|---|---|
| 3.5 | 0.12 |
| 3.6 | 0.29 |
| 3.7 | 0.13 |
| 3.8 | 0.07 |
| 3.11 | 0.12 |
| 3.12 | 0.10 |

Example 3.5, example 3.6, example 3.7, example 3.11 and example 3.12 showed good gel strength as compared to example 3.8.

2. Antimalarial Efficacy Study: Clinical Simulation Study

Method: The efficacy of the treatment was evaluated in a clinical simulation study, where the parasitemia was allowed to rise to 5-20% before commencement of treatment. Swiss male mice (25±5 g) were infected with donor blood infected with *P. berghei* ANKA. Example 3.11, example 3.12 and drug solution at $1/10^{th}$ of the therapeutic dose, marketed product at 100% therapeutic dose were administered by subcutaneous route once parasitemia count rose to 10-15%. Antimalarial activity was evaluated at 72 h and survival was monitored up to 12 days.

TABLE 10

Clinical simulation study protocol for example 3.11, example 3.12, artemether-lumefantrine solution (1/10$^{th}$ therapeutic dose) and for marketed product:

| No | Groups | Days | Dose of Arteether | Dose of Artemether | Dose of Lumefantrine |
|---|---|---|---|---|---|
| 1 | Control | — | — | — | — |
| 2 | Blank example 3.11 | Single dose on day zero | — | — | — |
| 3 | Example 3.11 (1/10 dose) | Single dose on day zero | — | 3.1 mg/kg (1/10) | 18.6 mg/kg (1/10) |
| 4 | Example 3.12 (1/10 dose) | Single dose on day zero | — | 3.1 mg/kg (1/10) | 18.6 mg/kg (1/10) |
| 5 | Marketed Product E-Mal | Three doses on day zero, one and two. | 31.0 mg/kg (100%) | — | — |
| 6 | Drug solution Artemether and lumefantrine | Single dose on day zero | — | 3.1 mg/kg (1/10) | 18.6 mg/kg (1/10) |

Figure 7:
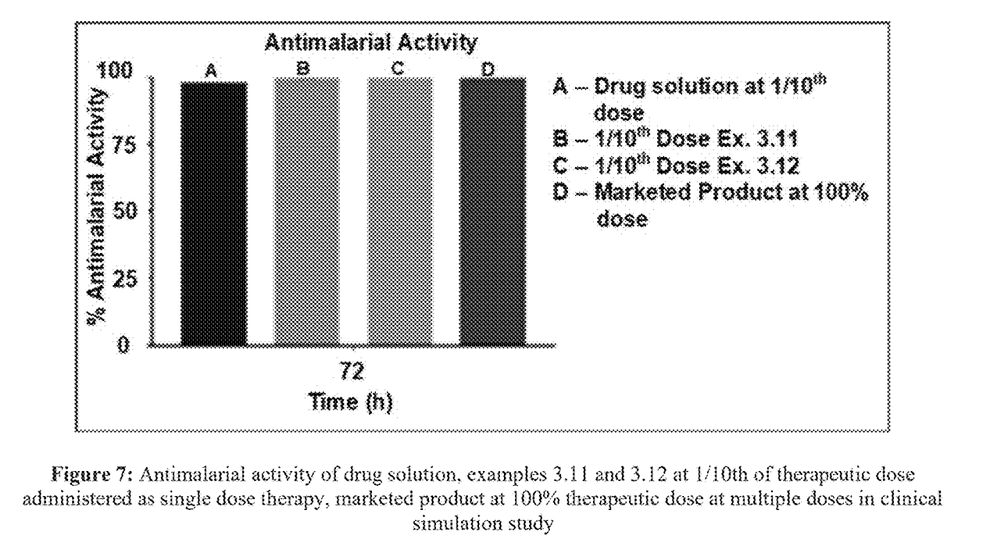
FIG. 7 shows antimalarial activity of drug solution, examples 3.11 and 3.12 at 1/10 of therapeutic dose administered as single dose therapy, marketed product at 100% therapeutic dose at three doses at 100% therapeutic dose in clinical simulation study.
Figure 8:
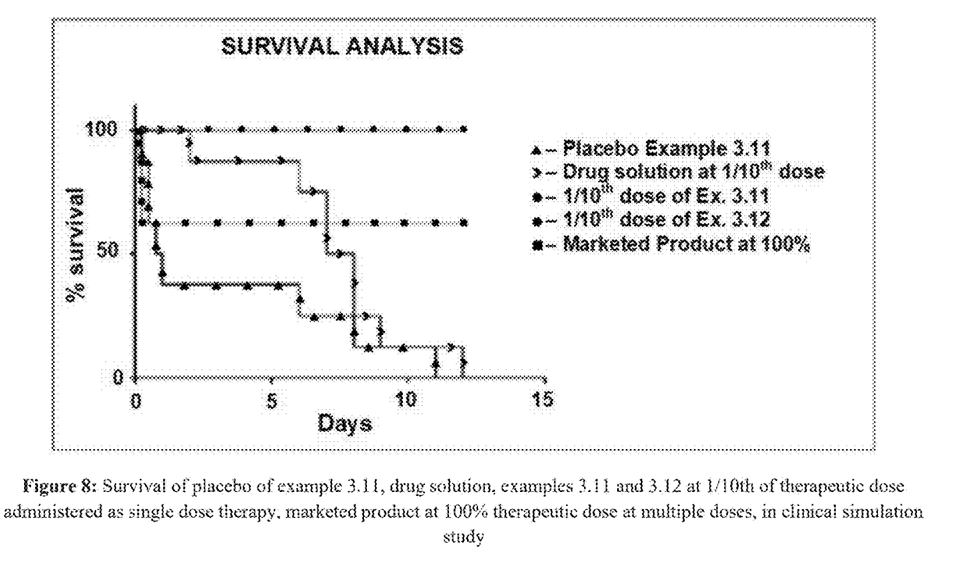
FIG. 8 shows survival of placebo example 3.11, drug solution, examples 3.11 and 3.12 at 1/10th of therapeutic dose administered as single dose therapy, marketed product at 100% therapeutic dose at three doses in clinical simulation study.

Example 3.12 and 3.11 showed comparable antimalarial activity at $\frac{1}{10}^{th}$ the therapeutic dose as a single dose therapy compared with Marketed product E-Mal (FIG. 7) at three doses of 100%. 100% survival was noted for example 3.11 and 3.12 at $\frac{1}{10}^{th}$ therapeutic dose given as a single dose therapy up to 12 days (FIG. 8). Drug solution at $\frac{1}{10}^{th}$ therapeutic dose showed recrudescence and lower of efficacy as compared to Examples 3.11 and 3.12 at the same dose when administered as a single dose therapy.

Drug solution at $\frac{1}{10}^{th}$ therapeutic dose showed recrudescence and lower of efficacy as compared to Examples 3.11 and 3.12 as the same dose when administered as a single dose therapy.

Example 4: Donepezil Injectable Compositions

TABLE 11

Compositions of Example 4:
Example 4

| Ingredients | 4.1 | 4.2 | 4.3 | 4.4 | 4.5 |
|---|---|---|---|---|---|
| Oleic Acid (mcL) | 0 | 0 | 250 | 0 | 250 |
| Polysorbate 80 (mcL) | 0 | 0 | 0 | 675 | 675 |
| N Methyl 2 Pyrrolidone (mcL) | 450 | 450 | 450 | 450 | 450 |
| PLGA (50:50); Resomer RG 502 (mg) | 0 | 130 | 130 | 130 | 130 |
| Donepezil base (mg) | 130 | 130 | 130 | 130 | 130 |
| Total (mcL) | 450 | 450 | 700 | 1125 | 1375 |
| Gel formation evaluation | | | | | |
| Gel formation at T = 0 h | No | Stiff implant Formation | Yes | Yes | Yes |
| Gel disintegration | 5 | 70 | 70 | 5 | 70 |

Preparation: PLGA and donepezil base were dissolved in NMP, followed by addition of Polysorbate 80 and/or oleic acid.

Figure 9:
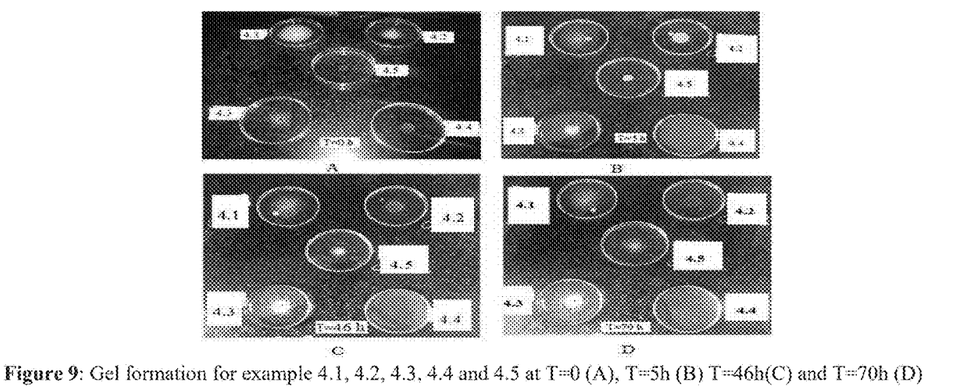
FIG. 9 are photographs depicting gel formation for example 4.1, 4.2, 4.3, 4.4 and 4.5 at T=0 (A), T=5 h (B) T=46 h (C) and T=70 h (D).

Method 3: 100 mcL of solution was added into a petri plate containing about 10-15 ml water at room temperature. Strength of the formed gel was evaluated based on visual observation for gel spreading and disintegration and photographs were taken initially and thereafter at 5, 46 and 70 h. (FIG. 9)

In Vitro Release Testing of Example 4

Figure 10:
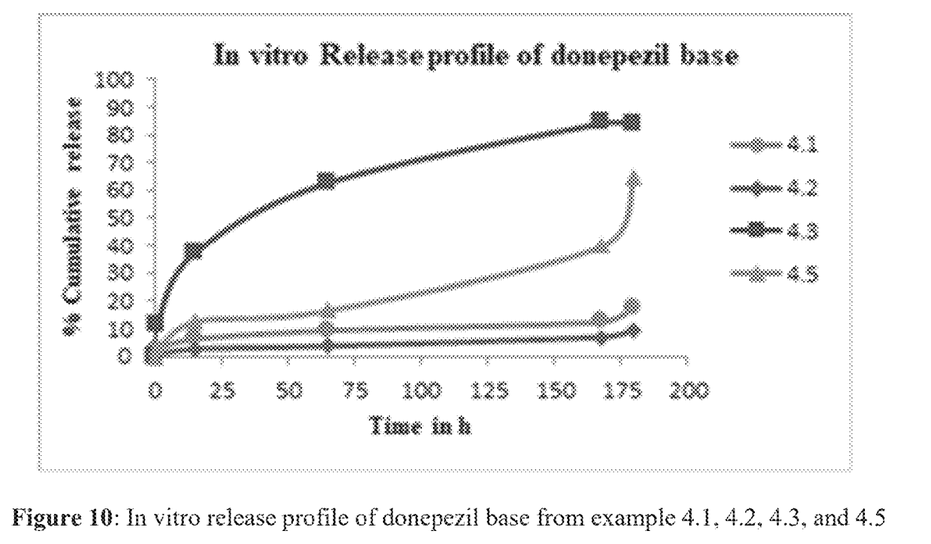
FIG. 10 is an in vitro release profile of donepezil base for compositions of Examples 4.1, 4.2, 4.3 and 4.5.

Example 4.1 (0.45 ml), example 4.2 (0.45 ml), example 4.3 (0.7 ml) and example 4.5 (1.2 ml) were added to half quantity of water (0.225 ml for example 4.1 and example 4.2, 0.35 ml for example 4.3 and 0.6 ml for example 4.5) filled in one side open cylindrical sample holder. Samples were stirred 20 times and allowed to equilibrate for 1 h. After one hour; sample holders were placed inside glass bottles. 500 ml media containing USP phosphate buffer (pH 7.4) (50 mM), 0.25% w/v SLS and 0.1% sodium azide was then added slowly and incubated at 40° C./75% RH stability chamber. Samples were taken at regular intervals and analyzed by UV at 315 nm for donepezil release. (FIG. 10)

TABLE 12

% Release of donepezil base from example 4.1, example 4.2, example 4.3 and example 4.5:
% Cumulative Release of Donepezil base
Example 4

| Time in (h) | 4.1 | 4.2 | 4.3 | 4.5 |
|---|---|---|---|---|
| 1 | 2.85 | 1.04 | 11.63 | 3.05 |
| 15 | 6.34 | 2.75 | 37.28 | 12.81 |
| 65 | 9.33 | 3.81 | 62.69 | 16.71 |
| 168 | 12.50 | 6.91 | 84.11 | 40.00 |
| 180 | 17.45 | 9.18 | 83.87 | 64.94 |

The invention claimed is:

1. An intramuscular or subcutaneous water-free self microemulsifying drug delivery system (SMEDDS), which is a unit dosage form of about 400-4000 mcL, consisting of:
   a) about 200-1200 mcL polyoxyethylene sorbitan ester;
   b) one or more selected from about 100-800 mcL oleic acid and about 100-1000 mcL benzyl benzoate;
   c) about 100-1200 mcL N-methyl pyrrolidone (NMP);
   d) about 7.5-30 mg arteether or artemether and about 45-180 mg lumefantrine;
   wherein the drug delivery system contains less than about 1 wt % moisture;
   wherein the drug delivery system is capable of forming a gel in situ in contact with water; and
   wherein the ratio of polyoxyethylene sorbitan ester to NMP is 1:0.6 to 1:1.

2. The drug delivery system of claim 1, containing less than about 0.5 wt % moisture.

3. The drug delivery system of claim 1 formulated as a unit dosage form which is administered as single or multiple dose therapy for prevention or treatment of malaria.

4. The drug delivery system of 1, which does not comprise dibutyl sebacate, 2-pyrrolidone polyglyceryldistearate (PGDS), or any combination thereof.

5. The drug delivery system of claim 1 wherein the gel strength of the drug delivery system is at least 0.07 mJ.

6. The drug delivery system of claim 4, wherein the drug delivery system is formulated as a unit dosage form for single or multiple dose therapy for the treatment of malaria.

7. A method of treating a subject suffering from a disease or disorder ameliorated by one or more active pharmaceutical ingredients, the method comprising administering the drug delivery system of claim 1, in an amount and for a period of time sufficient to treat the subject.

8. The method of claim 7, wherein the subject is a human.

9. The method of claim 8, wherein the drug delivery system is administered in a single or multiple dose which effectively treats the disease or disorder.

* * * * *